United States Patent [19]

Rubinstein et al.

[11] Patent Number: 4,971,080

[45] Date of Patent: Nov. 20, 1990

[54] PERMANENT WAVING AND HAIR CONDITIONING COMPOSITION

[75] Inventors: Arnold Rubinstein, Norwalk; Frances E. Erskine; Donna W. Bulakites, both of Fairfield; Ernest J. Klemm, Westport, all of Conn.

[73] Assignee: Shiseido Co. Ltd., Tokyo, Japan

[21] Appl. No.: 86,157

[22] Filed: Aug. 17, 1987

[51] Int. Cl.$^5$ .......................... A61K 7/09; A61K 7/11
[52] U.S. Cl. ...................................... 132/202; 132/207
[58] Field of Search ............................ 132/7, 202, 210

[56] References Cited

U.S. PATENT DOCUMENTS 1,515,854  11/1924  Foth ......................................... 132/7

OTHER PUBLICATIONS

Cosmetics by Sagarin 1957, p. 164.

*Primary Examiner*—V. Millin

*Attorney, Agent, or Firm*—Mattern, Ware, Stoltz & Fressola

[57] ABSTRACT

By incorporating corn syrup or glucose syrup into a conventional permanent hair waving solution, a unique permanent waving and hair conditioning composition is achieved which conditions the hair while simultaneously permanently waving the hair, in a single, one-step operation. In addition, the head of hair is permanently waved with a substantially lower level of damage occurring to the hair fibers than is otherwise encountered. Furthermore, by varying the relative quantity of corn syrup to the quantity of permanent wave solution, a variety of compositions are achieved for use on all different hair textures and levels of hair damage. However, in each instance, an effective amount of the carbohydrate mixture must be employed in order to ensure that the desired low level of damage to the hair is achieved.

11 Claims, No Drawings

PERMANENT WAVING AND HAIR CONDITIONING COMPOSITION

TECHNICAL FIELD

This invention relates to permanent waving compositions, more particularly to permanent waving compositions for simultaneously conditioning the hair while imparting a permanent wave thereto.

BACKGROUND ART

As is well known, hair is composed of a unique protein material, called "keratin", which is distinguished by the fact that it contains a very significant amount of an amino acid (cystine) which contains the element sulfur in addition to the elements nitrogen, oxygen, carbon and hydrogen. In the structure of hair, the cystine covalently links polypeptide chains, inter and intra molecularly, (K) through two sulfur atoms (S-S). These disulfide bonds can be broken only by specific chemical action.

Similarly, it is well established that in order to permanently wave hair this disulfide linkage must be broken. In this regard, many prior art compositions have been developed for the "cold permanent waving" of hair. Typically, these prior art systems treat the hair with a reducing agent which breaks the disulfide (cystine) linkages in the hair while the hair is wound around a curling rod.

The reducing agent typically employed is a mercaptan. The chemistry involved in the reaction of a mercaptan with the cystine disulfide bonds in the hair fiber is illustrated by the following chemical equation:

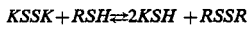

$$KSSK + RSH \rightleftharpoons 2KSH + RSSR$$

By rebonding the sites in the reduced keratin in their new curled configuration, a permanent set which is impervious to water is established.

The rebonding of the reduced sites is accomplished by the action of a chemical oxidizing agent, commonly referred to as the permanent wave neutralizer. Typically, the oxidizing agent used in most neutralizers is hydrogen peroxide, and its chemical reaction is illustrated in the following equation:

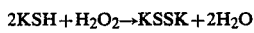

$$2KSH + H_2O_2 \rightarrow KSSK + 2H_2O$$

A problem encountered with the use of mercaptan reducing agents for the permanent waving of hair is that one lotion strength is needed for normal hair while a different lotion strength is needed for damaged or difficult to wave hair. This problem is further compounded when there is damaged as well as normal hair on a head of hair to be permanently waved.

In general, damaged hair fibers and relatively undamaged hair fibers coexist on almost every head. Since the hair grows outwardly from the scalp, it is constantly being subjected to mechanical damage, particularly from the normal grooming process of shampooing, combing, drying, and brushing. In addition to this physical damage of hair, hair is also damaged by chemical action such as by exposure to sunlight and contact with water containing chlorine. Also, the repeated use of permanent waving compositions on the hair fibers may cause damage to the hair especially if not used according to directions.

Damage to the hair fiber by other than chemical service is almost entirely directed against the hair cuticle. In shampooing, for example, it is the actual physical manipulation of the hair, rather than the shampoo itself, which causes the majority of the damage. In normal hair, which has six to seven cuticle layers at the new growth or scalp area, studies have shown that a normal shampoo process can break away the cuticle at the rate of 1 to 2.5 cuticles for every fifty treatments. Since it is not unusual for a woman to shampoo her hair every day, it is therefore possible that she could lose up to seven cuticle layers of her hair in five months.

Since hair normally grows approximately one-half inch each month, it is apparent that in five months, all of the hair longer than two and one-half inches would be denuded of the cuticle layer. In addition, since the cuticle comprises ten percent or more of the hair fiber, and a much higher percentage in fine hair, and is intended to act as a protective sheath about the cortex, its complete destruction represents formidable damage to the hair fiber. Once the hair fiber has lost part or all of its cuticle, it is classified as porous and readily absorbs any aqueous solution applied to it.

Bleached hair is particularly difficult for the successful application of cold permanent wave solutions because the bleached hair fibers have a substantially reduced cystine level and are usually very fragile. Bleached hair is often characterized as being dry, brittle, and overly coarse.

As a result, special precautions are usually taken to protect bleached hair when a permanent wave solution is to be applied. These conventional precautions include the application of a pre-conditioner before the permanent wave solution is applied, along with the use of a specially formulated permanent wave lotion.

Another prior art technique typically employed both for bleached hair as well as all types of hair where diverse conditions exist along the hair fibers is the use of end wraps. For most permanent wave applications, a tress of hair is wrapped about a cylindrical rod or curler. However, since difficulty is often encountered in wrapping the free ends of the hair tress on the curler, a small square or rectangular piece of paper, commonly referred to as "end wraps" are folded over the ends of the hair tress in order to make the hair more controllable and more easily rolled about the curler.

In an attempt to eliminate the inherent difficulty encountered from overprocessing and underprocessing the various segments of the hair during a permanent wave application, various conditioning compositions have been applied to the end wraps so that the ends of the hair fibers are treated separately, by coming directly in contact with the end wraps. Such compositions as oils, lanolins, diluted waving lotions, conditioners and vitamin compositions have all been employed in the end wraps in an attempt to prevent the undesirable overprocessing of the hair ends.

In addition, the use of permanent wave lotions may cause damage to the hair fibers especially if directions are not followed. As a result, uniform results become increasingly difficult the more frequently a particular head of hair is permanently waved.

In spite of the extensive effort directed to the protection of the hair ends and to bleached hair, as well as to conditioning of the hair fibers prior to applying cold permanent waving compositions, none of these prior art systems have achieved the desired results. In general, typical prior art cold permanent wave lotions have been unable to satisfy the diverse conditions which exist along the length of hair fiber and produce a uniform permanently waved head of hair, with minor increased damage. In general, depending upon the concentration of the lotion applied to the head of hair, particular segments of the hair are either underprocessed or overprocessed, with the adverse appearance resulting therefrom, while the hair fibers are further damaged.

Consequently, it is a principal object of the present invention to provide a single, cold permanent waving composition which simultaneously conditions the hair and produces a substantially uniform permanent wave throughout the head of hair regardless of the damaged condition of portions of the hair fiber.

Another object of the present invention is to provide a unique permanent cold waving composition having the characteristic features described above which substantially reduces the amount of increased damage to the hair fibers caused by the permanent wave lotion.

Another object of the present invention is to provide a unique permanent cold waving composition having the characteristic features described above which can be formulated for various types of damaged hair conditions, thereby assuring an even more effective, uniform permanent wave.

Another object of the present invention is to provide a cold permanent waving composition having the characteristics defined above which is applied easily and conveniently in a single application step, without requiring any special application techniques or extra steps or procedures.

Other and more specific objects will in part be obvious and will in part appear hereinafter.

DISCLOSURE OF THE INVENTION

The present invention overcomes all of the prior art drawbacks and limitations by incorporating into a conventional permanent waving solution a substantial quantity of corn syrup. By combining corn syrup, or a known equivalent thereof, with a conventional permanent waving solution, a completely new and unique permanent waving and conditioning composition is achieved.

It has been found that the corn syrup acts to protect the damaged hair fibers, and allows the permanent wave solution to act uniformly along the entire length of the hair fiber. In this way, substantially improved permanent wave results are obtained, while the hair fibers realize a substantially lower level of damage.

It has also been found that there is a direct proportional relationship between the amount of corn syrup required in the permanent waving/conditioning composition of this invention, and the successful permanent waving of increasingly damaged hair fibers. In general, by increasing the amount of corn syrup employed, relative to the quantity of permanent waving solution, the resulting composition is capable of simultaneously conditioning and permanently waving increasingly more difficult or more damaged hair fibers.

Corn syrup, which is also commonly known as "glucose syrup" or "starch syrup", is a concentrated solution of partially hydrolyzed starch containing principally dextrose and fructose, along with maltose and higher molecular weight saccharides. Corn syrup which contains between about 38% and 57% dextrose is commonly referred to as Type II corn syrup, and has been found to be the preferred grade of corn syrup for use in this invention. However, corn syrups containing between 20% and 90% dextrose may be used in accordance with the present invention without departing from the scope thereof.

In addition, other carbohydrates such as honey, maple syrup or molasses may be used instead of corn syrup. However, for consistent, optimum conditioning results, corn syrup is preferred.

Typically, corn syrup is formed by extracting the starch formed in the corn kernels and then partially hydrolyzing the starch. In general, about 50% of the corn kernel comprises starch, so that the requisite base material is abundant and relatively easily obtained.

In order to extract the starch from the corn kernels, the corn kernels are usually first soaked in warm water and then are milled, or broken apart without crushing the germs. Water is then added, causing the lighter germs to float and are thus removed. The remaining crushed kernels are ground into a meal, water is added, and the coarse hulls are removed by filtration through a screen. The residual mixture, which comprises starch and gluten is suspended in water and allowed to float through a long channel or trough. The heavier starch sinks to the bottom and is collected and dried.

The collected starch is then partially hydrolyzed, yielding a combination of monosaccharides, disaccharides and polysaccharides. Although the ratio of the various components may vary considerably, the resulting corn syrup generally comprises the composition shown in Table 1.

TABLE 1

| Composition of Corn Syrup | |
| --- | --- |
| Dextrose | 50–52% |
| Fructose | 42% min |
| Maltose | 1.5% |
| Isomaltose | 1.5% |
| Triose | Trace |
| Higher Saccharides | 3–5% |

It is generally agreed that bleached hair fibers present the most damaged hair condition for the successful application of a permanent waving solution. However, by employing the hair conditioning/permanent waving composition of the present invention, with corn syrup comprising between about 40% and 75% of the entire composition, bleached hair fibers are simultaneously conditioned and permanently waved in a single application.

With the amount of corn syrup employed for bleached hair representing the maximum level needed in the conditioning/permanent waving composition of the present invention, formulations for less damaged hair conditions were developed. In achieving these various formulations, it was universally found that as the level of damage exhibited by the hair fibers on a particular head declined, the amount of corn syrup required in the final composition also declined in a direct, proportional relationship.

Using the teaching of the present invention, a beautician is now able to assess the amount of damage a particular head of hair possesses, on an overall scale from no damage to the damage typically encountered with bleached heads of hair, and then, based upon this assessment, mix a conventional permanent waving solution with the precise amount of corn syrup which is needed for that particular head of hair. In this way, a "prescription formulated" conditioning/permanent waving composition is achieved quickly and easily by the beautician. Furthermore, a single conditioning/permanent waving composition is realized, which is capable of both permanently waving the head of hair and conditioning the head of hair to enable the hair fibers to receive the permanent wave solution efficiently and effectively, without incurring substantial further damage.

BEST MODE FOR CARRYING OUT THE INVENTION

As detailed above, the unique conditioning/permanent waving composition of the present invention is obtained by mixing the requisite amount of corn syrup, or equivalent carbohydrate mixture, with a conventional permanent waving lotion. Typically, cold permanent waving lotions contain ammonium thioglycolate or glyceryl monothioglycolate as the active waving agents. Other components are usually added to these lotions, such as wetting agents, conditioning agents, pH adjusting agents, and fragrances. Most cold permanent waving lotions are available in several different strengths, in order to accommodate the various types of hair and hair damage levels normally encountered in the salon.

In dealing with bleached hair, which usually suffers reduced cystine levels and is extremely fragile, most cold permanent waving lotions are formulated as mild as possible, and usually contains a substantial quantity of conditioning agents. The conventional cold permanent waving lotions then range in various increasingly stronger formulations, with the strongest formulation being for normal hair.

Regardless of which cold permanent wave lotion is desired or which strength level is employed, the addition of corn syrup, or an equivalent carbohydrate mixture, has been found to create a substantially improved product, achieving a one-step permanent waving and conditioning composition.

As has been discussed above, the amount of corn syrup which is required to obtain the desired conditioning effect and substantial reduction in additional hair fiber damage varies directly with the level of damage a particular head of hair possesses. Based upon the experiments we have run, we have determined the amount of corn syrup required for each of the five different hair types typically encountered. In Table 2, the results of our experiments are displayed, with the preferred range for the corn syrup, or equivalent mixture being shown for each different type of hair condition, along with the comparable range of permanent wave lotion needed to form the permanent waving/conditioning composition of the present invention.

TABLE 2

| Hair Type | Amount of Carbohydrate Mixture (ml) | Amount of Permanent Waving Lotion (ml) |
|---|---|---|
| Normal | 0.1–5 | 99.9–95 |
| Tinted | 10–20 | 90–80 |
| Frosted | 10–30 | 90–70 |
| Ultra Light | 30–50 | 70–50 |
| Bleached | 40–75 | 60–25 |

By employing the information provided in Table 2, a beautician is able to create a specific, "prescription formulated" conditioning and permanent waving composition for every different individual desiring a permanent wave. By merely assessing an individual's head of hair and determining which hair type the individual possesses, a beautician can then select, using the information in Table 2, the precise amount of carbohydrate mixture and permanent wave lotion needed for that particular head of hair. By mixing the requisite ingredients together, the beautician effectively creates an individualized conditioning and permanent waving composition which provides, in a single application, optimal conditioning of the hair, as well as permanent waving of the hair, without causing substantially increased damage to the hair.

By employing the conditioning and permanent waving composition of the present invention, it has been found that hair is left soft and manageable, with good luster and elasticity. In particular, these desirable qualities have been achieved with bleached hair, which is usually left dull, dry, difficult to manage, with poor elasticity and straw-like texture after permanent waving. However, by employing the teaching of this invention, these undesirable qualities have been virtually eliminated with bleached hair as well as all other hair types.

EXAMPLES

In order to prove the efficacy of the present invention, different hair types, namely regular hair, tinted hair, and bleached hair, were tested in a variety of alternate ways. In general, comparative tests were conducted using different processing times, different permanent waving lotions, and different relative amount of carbohydrate mixtures in combination with the permanent waving lotion. The results attained are detailed in the following specific examples.

In these examples, the amount of hair damage caused by the application of a permanent wave lotion and the amount of damage caused by the application the conditioning and permanent wave composition of the present invention are evaluated and compared by employing either the 20% index, the 10% index, or the difference between these indices before and after treatment. The 20% index and the 10% index are well known methods of expressing the amount of damage caused by any particular treatment.

In order to determine the 20% index for any treatment such as tinting, bleaching or permanent waving, the force required to stretch the hair fiber to 20% elongation before treatment is measured and the energy required to stretch the hair fiber to 20% elongation after the treatment is also measured. The 20% index is then expressed as the ratio of the energy measurement after treatment to the energy measurement before treatment. The 10% index is virtually identical, except that 10% elongation of hair fiber is measured instead of 20%.

In both indices, the lower the fraction, or resulting decimal number, the greater the damage that was caused by the particular treatment. In order to provide easily identifiable and readily understandable designations for various index numbers, industry accepted standards of damage were created for various ranges of index numbers. In Table 3, these accepted standards are presented.

TABLE 3

| Index Number Designations | |
|---|---|
| 1 | No Damage |
| 0.9–1.0 | Slight indication of damage |
| 0.8–0.9 | Some indication of damage |
| 0.7–0.8 | Definite indication of damage |
| 0.6–0.7 | Damaged |

Once a head of hair has been tinted or bleached, the damage caused to the hair fibers by the tinting or bleaching process usually becomes so significant that the 20% index or the 10% index has been found to be an insufficient measure of additional damage caused to the hair fiber by additional treatments, such as permanent waving. Consequently, the additional damage caused to the hair fibers by the application of both permanent waving lotions and conditioning and permanent waving compositions of this invention have been expressed and compared by employing the actual change in the measured index as opposed to the index number itself. In practice, this change or "delta" is expressed by determining the mathematical difference between the 20% index, or the 10% index, prior to the application of the permanent waving composition (i.e., the index obtained from the chemical treatment (if there was one prior to the permanent wave) and the 20% index, or 10% index, after the application of the permanent waving composition. In this way, the actual damage caused by the permanent waving process itself is expressed directly.

EXAMPLE I

Several samples of normal hair were permanently waved, using an ammonium thioglycolate permanent waving solution which was formulated for normal or regular hair. In addition, in order to see if processing time had any effect, the permanent wave lotion was allowed to remain on the hair fibers for three different lengths of time.

The same process was then employed on identical normal hair fibers using the identical ammonium thioglycolate permanent wave lotion combined with the carbohydrate mixture of the present invention. The resulting conditioning and permanent waving composition comprised a 5% concentration of the carbohydrate mixture.

In each case, the 20% index was determined and the results are shown in Table 4.

TABLE 4

| | Normal Hair | |
|---|---|---|
| Lotion | Perm Process Time (min) | 20% Index |
| Perm Lotion only | 20 | 0.772 |
| Perm and Carbohydrate Mixture (5%) | 20 | 0.817 |
| Perm Lotion only | 40 | 0.751 |
| Perm and Carbohydrate Mixture (5%) | 40 | 0.765 |
| Perm Lotion only | 60 | .729 |
| Perm and Carbohydrate Mixture (5%) | 60 | .773 |

As can be seen from the results of the 20% index shown in Table 4, the application of the conditioning and permanent waving composition of the present invention employing a 5% concentration of carbohydrate mixture resulted in a significant reduction in the amount of damage caused by the permanent waving application, regardless of the processing time employed.

EXAMPLE II

In order to determine the efficacy of the present invention when applied to the tinted hair, the same process detailed above was employed in permanent waving various tinted hair fibers. However, in order to employ a typical permanent wave lotion commonly used with tinted hair, the permanent wave lotion used in this experiment was an ammonium thioglycolate permanent wave lotion specifically formulated for tinted hair.

For purposes of consistency, the conditioning and permanent waving composition of the present invention comprised a 5% concentration of the carbohydrate mixture, as was done with the normal hair detailed above. The results obtained from the various tests are detailed in Table 5.

TABLE 5

| | Tinted Hair | |
|---|---|---|
| Lotion | Perm Process Time (min) | Damage from Perm |
| Perm Lotion only | 12 | 0.280 |
| Perm and Carbohydrate Mixture (5%) | 12 | 0.215 |
| Perm Lotion only | 30 | 0.282 |
| Perm and Carbohydrate Mixture (5%) | 30 | 0.242 |
| Perm Lotion only | 60 | 0.273 |
| Perm and Carbohydrate Mixture (5%) | 60 | 0.226 |

As is clearly apparent from the results detailed in Table 5, substantially less damage was caused to the hair fibers when the carbohydrate mixture was combined with the permanent wave lotion, regardless of the process time employed.

The data found in Table 5 clearly indicates that significant protection was afforded to the hair strands permed with a mixture of the permanent wave lotion and the carbohydrate mixture. In addition, it is important to note that this significant protection resulted with only a 5% concentration of the carbohydrate mixture, even through the preferred concentration of the carbohydrate mixture for tinted hair is between about 10% and 20%.

EXAMPLE III

Another group of tests were performed on tinted hair in order to show the effect of using different concentrations of the carbohydrate mixture of the present invention with a permanent wave lotion. The results of these tests are detailed in Table 6.

In these tests, an acid balanced permanent wave lotion formulated for regular hair was employed, first independently and then with different concentrations of the carbohydrate mixture. Prior to conducting any of these tests, hair fibers were tinted three times using a conventional hair tinting preparation.

TABLE 6

| | Tinted Hair | | |
|---|---|---|---|
| Relative Concentration of Perm Lotion and Carbohydrate Mixture. | Perm Process Time (Min) | 10% Index | Damage From Perm |
| Perm Lotion only | 15 | 0.568 | 0.189 |
| 75% Perm Lotion and 25% Carbohydrate Mixture | 15 | 0.677 | 0.133 |
| 50% Perm Lotion and 50% Carbohydrate Mixture | 15 | 0.637 | 0.100 |

By reviewing the results obtained in Table 6, it is readily apparent that substantial protection is provided to the hair fibers when the carbohydrate mixture of the present invention is combined with the permanent waving lotion. In addition, it is readily apparent that the use of a 25% carbohydrate mixture is sufficient to provide substantial protection to the hair fibers. Although greater protection is afforded by a 50% carbohydrate mixture, the amount of increase in protection provided by a 50% carbohydrate mixture is not proportionally as great as is provided by the addition of a 25% carbohydrate mixture over a 100% permanent wave lotion. Consequently, these results clearly show that substantial protection is afforded to tinted hair with the use of substantially less carbohydrate mixture than is required for bleached hair.

EXAMPLE IV

Various tests were performed on bleached hair in accordance with the present invention and the results are detailed in Table 7. As shown therein, different concentrations of the carbohydrate mixture were employed in combination with an ammonium thioglycolate permanent wave lotion formulated for regular hair. In addition, tests were also conducted employing the carbohydrate mixture along with an ammonium thioglycolate permanent wave lotion formulated for tinted hair.

Furthermore, in order to assure that the use of the conditioning and permanent waving composition of the present invention does impart protection to the hair, the tests detailed in Table 7 were exaggerated by bleaching the hair fibers on which the experiments were conducted to a highly damaged state. As a result, any benefit that is obtained on hair fibers of this highly damaged condition would be indicative of the minimum type of benefit to be derived from employing the conditioning and permanent waving composition of the present invention.

TABLE 7

| Lotion | Bleached Hair | | |
|---|---|---|---|
| | Bleach Exposure (hrs) | Process Time (min) | Damage from Perm |
| Perm Lotion (Reg) | 2 | 4 | 0.367 |
| Perm Lotion (Reg) & Carbohydrate Mixture (5%) | 2 | 4 | 0.285 |
| Perm Lotion (Tinted) | 2 | 4 | 0.320 |
| Perm Lotion (Tinted) & Carbohydrate Mixture (5%) | 2 | 4 | 0.243 |
| Perm Lotion (Reg) | 2 | 5 | 0.310 |
| Perm Lotion (Reg) & Carbohydrate Mixture (50%) | 2 | 5 | 0.228 |
| Perm Lotion (Reg) | 1 | 5 | 0.314 |
| Perm Lotion (Reg) & Carbohydrate Mixture (50%) | 1 | 5 | 0.188 |

As is apparent from the result shown in Table 7, significant protection is imparted to the hair by incorporating the carbohydrate mixture into the waving lotion. In addition, by employing a conditioning and permanent waving composition which comprises 50% of a carbohydrate mixture, substantial protection of the hair fibers is realized, particularly in hair fibers that were less severely damaged by the bleaching process.

EXAMPLE IV

In Table 8, the results obtained from further tests on bleached hair fibers are shown. In these tests, an acid balanced permanent wave lotion formulated for regular hair was employed, both independently and with different concentrations of the carbohydrate mixture in accordance with the present invention. Furthermore, hair fibers bleached for one hour as well as two hours were employed, in order to show the efficacy of the present invention on hair fibers of a highly damaged condition.

TABLE 7

| Relative Concentration of Perm Lotion and Carbohydrate Mixture | Bleached Hair | | | |
|---|---|---|---|---|
| | Perm Process Time (Min) | Exposure to Bleaching | 10% Index | Damage From Perm |
| Perm Lotion only | 5 | 1 hour | 0.493 | 0.149 |
| 75% Perm Lotion and 25% Carbohydrate Mixture | 5 | 1 hour | 0.512 | 0.121 |
| 50% Perm Lotion and 50% Carbohydrate Mixture | 5 | 1 hour | 0.518 | 0.089 |
| Perm Lotion only | 5 | 2 hours | 0.357 | 0.192 |
| 75% Perm Lotion and 25% Carbohydrate Mixture | 5 | 2 hours | 0.394 | 0.161 |
| 50% Perm Lotion and 50% Carbohydrate Mixture | 5 | 2 hours | 0.454 | 0.109 |

By reviewing the results obtained in Table 8, it is readily apparent that the combination of a carbohydrate mixture with the permanent waving lotion provides increased protection to the hair fibers, regardless of whether the hair fibers had been bleached for one hour or for two hours. In addition, it is readily apparent that although protection is afforded to the hair fibers by a 25% carbohydrate mixture, substantially greater protection is provided when equal amounts of the carbohydrate mixture is combined with the permanent wave lotion to form the permanent waving and conditioning composition in accordance with the present invention. With this composition, substantially less damage is caused to the hair fibers, regardless of their original condition, with the hair fibers being permanent waved into a very manageable and desirable state.

It will thus be seen that the objects set forth above, among those made apparent from the preceding description, are efficiently attained and, since certain changes may be made in the above composition without departing from the scope of the invention, it is intended that all matter contained in the above description shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Particularly, it is to be understood that in said claims, ingredients or compounds recited in the singular are intended to include compatible mixtures of such ingredients wherever the sense permits.

Having described my invention, what I claim as new and desire to secure by Letters Patent is:

1. A combined conditioning and permanent waving composition for application directly to a head of hair to impart a substantially uniform permanent wave thereto, while simultaneously conditioning the hair and reducing the damage caused by the permanent wave lotion, such composition comprising between about 0.1% and 75% of a carbohydrate mixture and a cold permanent waving lotion forming the balance.

2. The combined conditioning and permanent waving composition defined in claim 1, wherein said carbohydrate mixture is further defined as comprising corn syrup or glucose syrup.

3. The combined conditioning and permanent waving composition defined in claim 2, wherein said corn syrup is further defined as containing between about 20% and 90% dextrose.

4. The combined conditioning and permanent waving composition defined in claim 3, wherein said corn syrup is further defined as comprising a Type II corn syrup incorporating between about 38% and 57% dextrose.

5. The combined conditioning and permanent waving composition defined in claim 2, wherein said corn syrup is further defined as comprising a combination of dextrose, fructose, maltose, isomaltose, triose, and higher molecular weight saccharides.

6. The combined conditioning and permanent waving composition defined in claim 1, wherein said composition is further defined as being formulated for normal hair and said carbohydrate mixture comprises between about 0.1% and 5% of the final composition.

7. The combined conditioning and permanent waving composition defined in claim 1, wherein said composition is further defined as being formulated for tinted hair, and said carbohydrate mixture comprises between about 10% and 20% of said composition.

8. The combined conditioning and permanent waving composition defined in claim 1, wherein said composition is further defined as being formulated for frosted hair, and said carbohydrate mixture comprises between about 10% and 30% of said composition.

9. The combined conditioning and permanent waving composition defined in claim 1, wherein said composition is further defined as being formulated for ultra light hair, and said carbohydrate mixture comprises between about 30% and 50% of said composition.

10. The combined conditioning and permanent waving composition defined in claim 1, wherein said composition is further defined as being formulated for bleached hair, and said carbohydrate mixture comprises between about 40% and 75% of said composition.

11. A method for formulating a combined permanent waving and conditioning composition specifically for a particular head of hair, comprising the steps of:
   A. assessing the level of damage present in the head of hair to be permanently waved and determining the relative damage of the particular head of hair as compared to a highly bleached head of hair;
   B. determining the amount of carbohydrate mixture required based upon the relative level of damage to the head of hair to be permanently waved by selecting said amount from between 0.1% and 75% of the entire composition, with the greater amount being employed for the more damaged heads of hair;
   C. combining a conventional cold permanent waving lotion with the desired predetermined relative quantity of the carbohydrate mixture to attain the desired prescription formulated combined conditioning and permanent waving composition; and
   D. applying said combined conditioning and permanent waving composition to the particular head of hair in the conventional manner, thereby obtaining the desired permanently waved head of hair with a substantially reduced level of damage being realized by the hair fibers.

* * * * *